(12) United States Patent
Yun et al.

(10) Patent No.: US 9,907,636 B2
(45) Date of Patent: Mar. 6, 2018

(54) CURING LIGHTS WITH HOMOGENOUS LIGHT PATCH

(71) Applicant: 3M INNOVATIVE PROPERTIES COMPANY, St. Paul, MN (US)

(72) Inventors: Zhisheng Yun, Woodbury, MN (US); Rudolf Schmid, Eichenau (DE); James L. Graham, II, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 173 days.

(21) Appl. No.: 14/789,224

(22) Filed: Jul. 1, 2015

(65) Prior Publication Data

US 2017/0002993 A1  Jan. 5, 2017

(51) Int. Cl.
*A61C 13/15* (2006.01)

(52) U.S. Cl.
CPC .................................. *A61C 19/003* (2013.01)

(58) Field of Classification Search
CPC .......... A61C 19/003; G02B 2003/0093; G02B 27/0911; G02B 3/0062; G02B 3/0056
USPC ............... 359/621–623; 355/1; 362/259, 573
See application file for complete search history.

(56) References Cited

U.S. PATENT DOCUMENTS

| | | | | |
|---|---|---|---|---|
| 4,168,900 | A * | 9/1979 | Adachi | G02B 3/0012 355/1 |
| 4,350,431 | A * | 9/1982 | Mochizuki | G02B 3/0062 355/1 |
| 6,746,124 | B2 | 6/2004 | Fischer | |
| 7,273,369 | B2 | 9/2007 | Rosenblood | |
| 7,821,718 | B1 * | 10/2010 | Govyadinov | G02B 27/0944 359/622 |
| 2004/0156130 | A1 | 8/2004 | Powell | |
| 2005/0105189 | A1 * | 5/2005 | Mikhailov | G02B 6/4204 359/641 |
| 2006/0199144 | A1 | 9/2006 | Liu | |
| 2006/0275732 | A1 | 12/2006 | Cao | |

(Continued)

FOREIGN PATENT DOCUMENTS

EP  1708008  10/2006
GB  2454860  5/2009

(Continued)

OTHER PUBLICATIONS

Hecht, Eugene. Optics. Hecht. 4th ed. Reading, MA: Addison-Wesley, 1998. 152. Print.*

(Continued)

*Primary Examiner* — Sean Gramling
*Assistant Examiner* — Gerald J Sufleta, II (57) ABSTRACT

A light irradiation device that emits a light patch of uniform intensity. The device may be a dental light wand. The device has a light source, a lenslet array and an optional relay lens. The light source may be a laser or a collimated LED. Each lenslet of the lenslet array has two convex surfaces, a front convex surface, and a rear convex surface that is opposite to the front convex surface. The front convex surface has a focal point on the principal plane of the rear convex surface. The focal length of the front convex surface differs from the focal length of the rear convex surface. Light beams emitted by the light source pass through the lenslet array, and if a relay lens is present then pass through the relay lens, forming a light patch of uniform intensity.

13 Claims, 5 Drawing Sheets

(56) References Cited

U.S. PATENT DOCUMENTS

| | | |
|---|---|---|
| 2007/0128577 A1 | 6/2007 | Scott |
| 2010/0149222 A1 | 6/2010 | Welford et al. |
| 2012/0075686 A1* | 3/2012 | Hudman .............. G02B 26/101 |
| | | 359/205.1 |
| 2012/0192919 A1 | 8/2012 | Mizuyama |
| 2013/0017508 A1 | 1/2013 | Mace |
| 2014/0168615 A1 | 6/2014 | Sato et al. |
| 2014/0177022 A1 | 6/2014 | Saisho et al. |

FOREIGN PATENT DOCUMENTS

| | | |
|---|---|---|
| WO | WO 2007/141185 | 12/2007 |
| WO | WO 2012/117363 | 9/2012 |
| WO | WO 2012/122455 | 9/2012 |

OTHER PUBLICATIONS

Linos, "Introduction to Laser beam Homogenizer" 1 pp. [retrieved from the internet on Aug. 13, 2015], URL <http://www.google.com/url?sa=t&rct=j&q=&esrc=s&frm=1&source=web&cd=1&ved=0CB4QFjAAahUKEwjJw6C1mbjHAhWluYAKHZcWD2c&url=http%3A%2F%2Fwww.linos.com%2Fpages%2Fmediabase%2Foriginal%2FIntroduction_Homogenizer_7448.pdf&ei=ERDWVYn3AojzggSXrby4Bg&usg=AFQjCNHF5zCFG-7hMPMTgySZAeYM4sobkA>.

Precoptic, "Eclipse Ni-E", [retrieved form the internet on May 6, 2015], URL <http://www.precoptic.pl/Products/5/18/ECLIPSE-Ni-E-inteligentny-zau>, 5 pgs.

Suss, "Strategies for Beam Homogenizing", 5 pgs., Jan. 2006.

Voelkel, "Laser Beam Homogenizing: Limitations and Constraints," Proc. SPIE, 2008, vol. 7102, pp. 71020J-1-71020J-12.

Zemax, "Fly's Eye Arrays Uniform Illumination in Digital Projector Optics," 2013, 9 pgs.

Cumme, M. et al., "From regular periodic micro-lens arrays to randomized continuous phase profiles," Advanced Optical Technologies, vol. 4, pp. 47-61, Feb. 2015.

International Search Report for PCT/US2016/039718, dated Sep. 12, 2016.

* cited by examiner

CURING LIGHTS WITH HOMOGENOUS LIGHT PATCH

BACKGROUND

Light-curable or light-hardenable materials are widely used in dentistry for the restoration of teeth, for example for filling a cavity in a tooth. Such materials typically can be made to provide optical characteristics that resemble those of natural teeth, which makes those materials a favored alternative to unpleasant looking amalgam materials.

Light-hardenable materials may initially be generally soft or flowable so that they can be applied in a desired location and shaped to a desired contour. For example, for restoration of a tooth the dental material may be filled into a tooth cavity and shaped so that the restored tooth resembles a natural tooth. Once the desired shape has been formed, the material may be hardened by exposing it to light of a specific wavelength and for a specific time duration. Commonly the wavelengths for such curing light fall between 300 nm and 500 nm.

Handheld dental light irradiation devices are widely used for hardening such materials. However, the devices currently available on the market do not produce a light patch of uniform intensity at the restoration site.

To achieve even and uniform curing of the dental materials at the restoration site, it is desirable to provide a light irradiation device that emits a light patch of uniform intensity at the restoration site.

SUMMARY

A first light irradiation device for emitting a light patch of uniform intensity, consistent with the present invention, includes a housing, a light source within the housing emitting light beams, and an array of transparent lenslets within the housing. Each of the lenslets of the array has a front convex surface and a rear convex surface opposite the front convex surface. The front convex surface has a focal point having a first focal length, f1, on a principal plane of the rear convex surface. The rear convex surface has a second focal point having a second focal length, f2, and f1 is different from f2. The light beams enter the transparent lenslets at the front convex surface and exit the transparent lenslets at the rear convex surface, forming a light patch of uniform intensity.

A second light irradiation device for emitting a light patch of uniform intensity, consistent with the present invention, includes a housing, a light source within the housing emitting light beams, a relay lens having a front relay lens surface and a rear relay lens surface opposite the front relay lens surface, and an array of transparent lenslets within the housing. Each of the lenslets of the array has a front convex surface and a rear convex surface opposite the front convex surface. The front convex surface has a first focal point having a first focal length, f1, on a principal plane of the rear convex surface. The rear convex surface has a second focal point having a second focal length, f2, and f1 is different from f2. The light beams enter the transparent lenslets at the front convex surface and exit the transparent lenslets at the rear convex surface. The light beams exit the lenslets and enter the relay lens at the front relay lens surface and exit the relay lens at the rear relay lens surface, forming a light patch of uniform intensity.

BRIEF DESCRIPTION OF THE DRAWINGS

The accompanying drawings are incorporated in and constitute a part of this specification and, together with the description, explain the advantages and principles of the invention.

DETAILED DESCRIPTION

Figure 1:
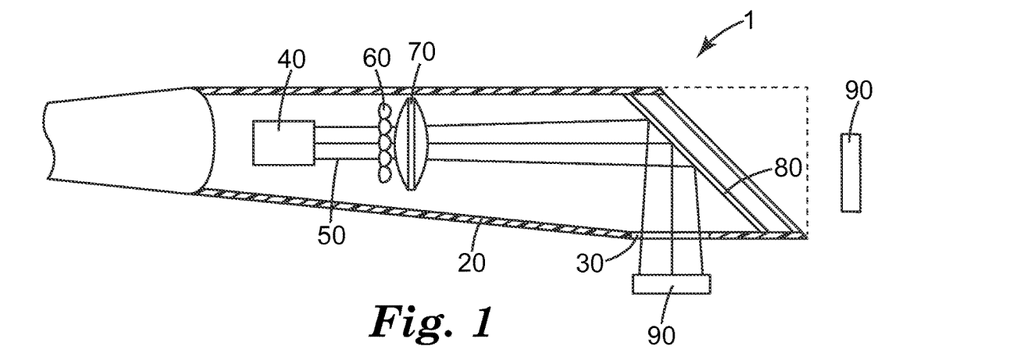
FIG. 1 is an exposed side view of an embodiment of the dental light irradiation device.

FIG. 1 shows an exposed side view of an embodiment of the dental light irradiation device. The device 1 has a housing 20 that forms an elongated body, a cover glass 30 covering an opening for light to exit, a light source 40, a lenslet array 60, a relay lens 70, and a light deflecting mechanism 80.

Light beams 50 produced by the light source 40 pass through the lenslet array 60. Light beams 50 then pass through the relay lens 70. Light beams 50 then are deflected by the light deflecting mechanism 80. Light beams 50 then exit the cover glass 30, and form a light patch 90 at a restoration site such as a tooth or a crown. The light patch 90 is a real image of the entrance aperture of lenslet array 60.

Figure 1A:
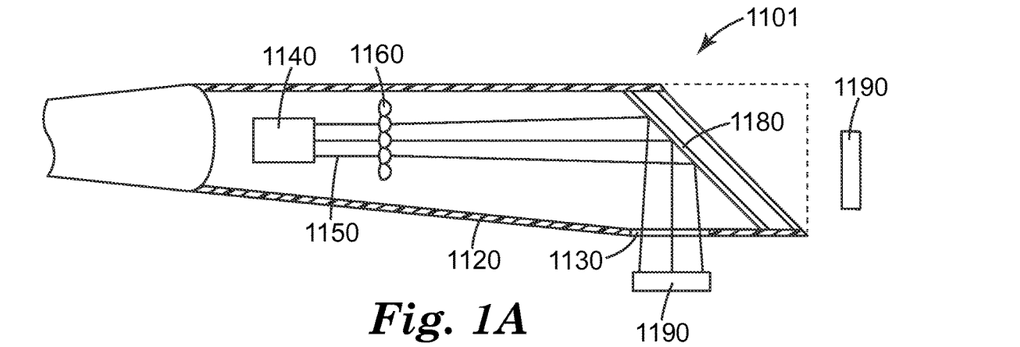
FIG. 1A is an exposed side view of an embodiment of the dental light irradiation device.

FIG. 1A shows an exposed side view of another embodiment of the dental light irradiation device. The device 1101 has a housing 1120 forming an elongated body, a cover glass 1130 covering an opening for light to exit, a light source 1140, a lenslet array 1160, and a light deflecting mechanism 1180.

Light beams 1150 produced by the light source 1140 pass through the lenslet array 1160. Light beams then are deflected by the light deflecting mechanism 1180, exit the cover glass 1130, and form a light patch 1190 at a restoration site such as a tooth or a crown. The light patch 1190 is a real image of the entrance aperture of lenslet array 1160.

Figure 1B:
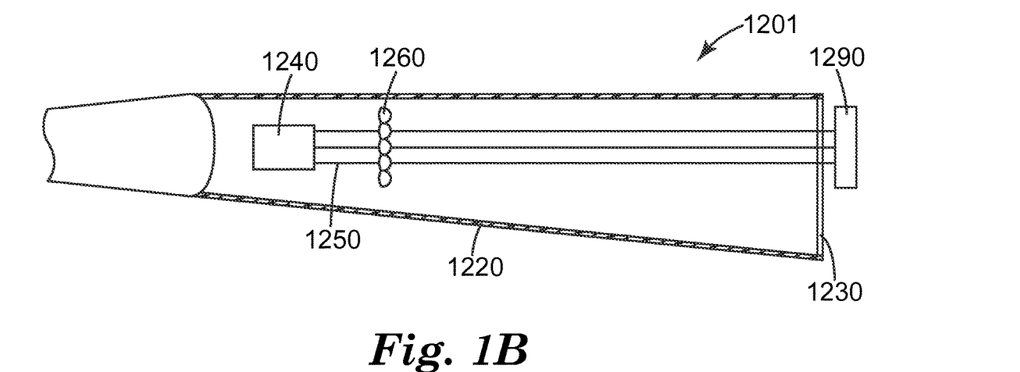
FIG. 1B is an exposed side view of an embodiment of the dental light irradiation device.

FIG. 1B shows an exposed side view of another embodiment of the dental light irradiation device. The device 1201 has a housing 1220 forming an elongated body, a cover glass 1230 covering an opening for light to exit, a light source 1240, a lenslet array 1260.

Light beams 1250 produced by the light source 1240 pass through a lenslet array 1260. Light beams then exit the cover glass 1230, and form a light patch 1290 at a restoration site such as a tooth or a crown. The light patch 1290 is a real image of the entrance aperture of lenslet array 1260. Optionally a relay lens (not shown) may be placed at a location in between the relay lens 1260 and the cover glass 1230, similar to the embodiment in FIG. 1.

The dental light irradiation device may be a handheld device, or a desktop device. It may be used intraorally on a tooth during a restoration procedure, or in a laboratory setting such as building a crown. The device may be battery powered, and the battery may be rechargeable. The device may also be powered by alternative means such as an adaptor cord plugged into a common AC power outlet.

The dental light irradiation device may employ a light source having a wavelength within a range of about 430 nm (nanometers) and about 490 nm and a peak wavelength within a range of about 444 nm and 453 nm. Further such light source preferably substantially does not comprise light at wavelengths outside the range of about 430 nm and about 490 nm. For example at least 90%, more preferably 95% of the light quantity emitted from the device is formed by light having a wavelength within a range of about 430 nm and about 490 nm.

The light source may be halogen, light-emitting diode (LED), plasma arc curing (PAC), or laser. The light source may be formed by a single high-power LED having an input power of between 6 W to 12 W and an optical output power of between about 1 W to about 3 W, preferably at least about 1.12 W. Further the light source may essentially form a point source.

Preferably, the light source is a collimated light-emitting diode (LED) or a laser. The light collimating means are preferably adapted and arranged relative to the light source to collimate light beams into a substantially parallel light beams. The skilled person will be able to select appropriate combinations of a light collimating means and a light source depending on the angle of radiation of the light source, the collimating characteristics of the light collimating means and the distance between the light source and the light collimating means. For example, such a light collimating means may comprise or may be formed of a lens. The lens may be a TIR lens or a plano-convex lens. In case a plano-convex lens is used the lens is preferably oriented with the planar side toward the light source. Preferably the light collimating means—although optionally comprising other optical means—comprises a single lens only. Further this single lens is preferably a plano-convex lens which convex side is aspherical.

The housing of the dental light irradiation device may be made out of a light impermeable material, such material can be metal, alloy, plastic, etc. The cover glass may be made out of a transparent material, such material can be plastic, glass, etc.

The light deflecting mechanism in any of the applicable embodiments may be a fold mirror or a 45 degree right angle prism. The fold mirror can be either a polished metal mirror, a plastic metal coated or a plastic dielectric multiple-layers coated mirror.

Figure 2:
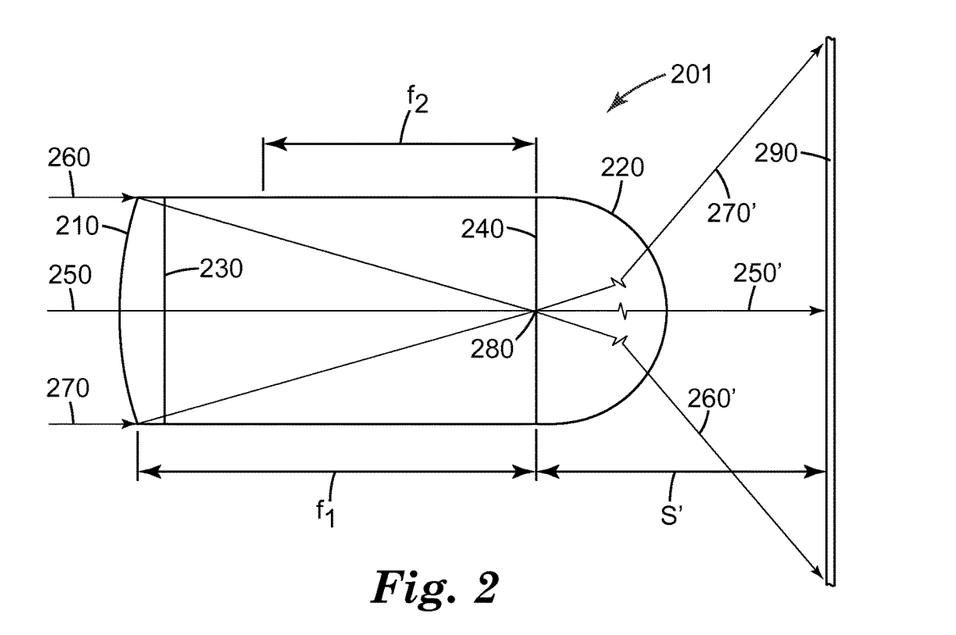
FIG. 2 is a side view of a lenslet.

FIG. 2 shows a side view of a lenslet 201. Lenslet array used in the dental light irradiation device may be composed of more than one lenslets. The lenslets may be identical to one another, or may be different from one another.

A lenslet 201 typically is made from a transparent material, with a refractive index greater than 1. The material may be optical glass or plastic, or any other type of suitable transparent material.

The lenslet 201 may have a square or rectangular cross-sectional shape, also known as aperture. The square or rectangular shape have straight edges and advantageously eliminates air gaps between adjacent lenslets when the lenslets are formed into an array. Alternatively the aperture may be in other geometric shapes with various numbers of straight edges such as triangle, rhombus, pentagon, hexagon, etc. Non-straight edge shapes may also be possible, such as round, oval, etc, or a combination of straight and non-straight edges such as half-circle.

The lenslet 201 has two surfaces that are opposite to each other, and the two surfaces of the lenslet 201 may be both spherical. In the example in FIG. 2, lenslet 201 has two convex surfaces that are opposite to each other: a front convex surface 210 and a rear convex surface 220.

Light beams emitted by the light source are incident upon the front convex surface 210. Exemplary light beams 250, 260, 270 are emitted by the light source and travel along substantially parallel paths and enter the front convex surface 210. Light beams then exit lenslet 201 respectively as 250', 260' and 270'.

Light beams 260 and 270 are incident upon the upper and lower edges of the front convex surface 210. Front convex surface 210 focuses the light beams and the light beams converge on the focal point 280 of the front convex surface 210. Light beams then diverge from the focal point 280 and exit the rear convex surface 220 as 260', 270'. Light beam 250 travels along the optical axis of the lenslet and retains its original path travelling through lenslet 201 and exiting lenslet 201 as 250'. The divergence of light beams magnifies the dimensions of the entrance aperture of the lenslet 201 at the lenslet's front surface 210 and forms a real image as a light patch 290 at distance S' from the rear convex surface.

The focal point 280 of the front convex surface 210 is located on the principal plane 240 of the rear convex surface 220. In other words the focal plane of front convex surface 210 is the same as the principal plane of rear convex surface 220. This configuration allows the front convex surface 210 to focus the light beams 250, 260, 270 to a focal point 280 within the lenslet itself and then diverge the light beams from the focal point without alterations in their divergent paths by the rear convex surface 220. In other words the original divergent paths of the light beams are unaffected by the rear convex surface 220, and the rear convex surface 220 does not alter the divergent paths of the light beams.

There are several advantages to preserving the original divergent paths of the light beams. When more than one lenslets like lenslet 201 are formed into a lenslet array, light beams that are incident at substantially the same angle upon the front convex surfaces of all the lenslets will exit the lenslet array along paths substantially parallel to each other. As explained in the rest of this patent application this allows for well-defined edges in the resulting composite light patch created by the lenslet array.

Lenslet 201 creates a light patch 290 at a distance S' from the rear convex surface 220 as a real image of the entrance aperture of lenslet 201. In other words the rear convex surface 220 relays the aperture of the lenslet 201 to a distance S'. S' is measured from the principal plane of the rear convex surface 220, and is the distance where the resulting image is in focus. Lenslet 201 does not image the light source to infinity. Because the longitudinal length of lenslet 201 is small, S' can also be approximately measured from the apex of the rear convex surface 220.

The front convex surface 210 has a focal length of f1. The rear convex surface 220 has a focal length of f2. The front convex surface 210 and the rear convex surface 220 are different from each other. In other words the front convex surface 210 and the rear convex surface 220 are not identical to each other. Focal length f1 of the front convex surface 210 and focal length f2 of the rear convex surface 220 have the following relationship:

$$0 < f1/2 < f2 < f1$$

In other words one half f1 is greater than zero and less than f2, and f2 is less than f1. This relationship determines the magnitude of the distance S'.

For example, there may be a pre-set overall length for the dental light irradiation device, and the light patch produced by the dental light irradiation device must fall on a tooth surface located immediately outside the cover window of the irradiation device. The focal lengths of the surfaces of the lenslet can be designed and adapted to ensure the resulting light patch is formed outside the dental light irradiation device and on the desired target.

The following equation illustrates the relationship between S' and the focal lengths f1 and f2:

$$1/f2 - 1/f1 = 1/S'$$

The radius of curvature R2 of the rear convex surface 220 may be smaller than the radius of curvature R1 of the front convex surface 210. R1 may be 0.05 mm to 50 mm, and R2 may be 0.05 mm to 50 mm. Radius is related to focal length and can be determined by the following equation:

$$f1 = (1/(n-1))R1$$

$$f2 = (n/(1-n))R2$$

Where R1 is the radius of curvature of the front convex surface 210, R2 is the radius of curvature of rear convex surface 220, and n is the refractive index of the lens material.

Figure 3A:
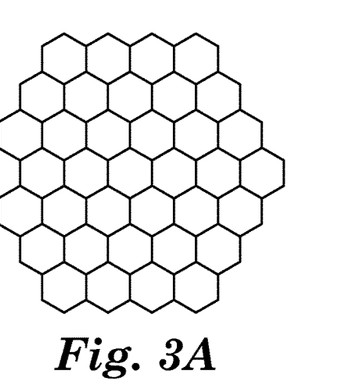
FIG. 3A is a top view of a lenslet array.
Figure 3B:
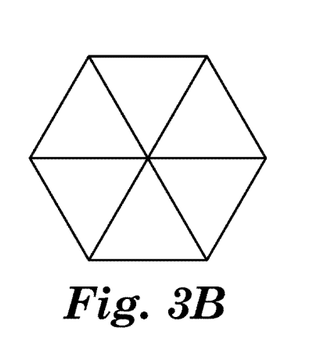
FIG. 3B is a top view of an alternative lenslet array.
Figure 3C:
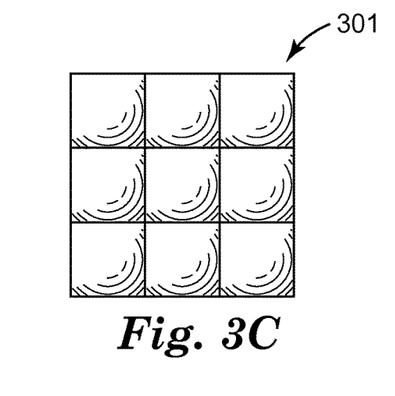
FIG. 3C is a top view of an alternative lenslet array.

FIG. 3C shows a top view of a two dimensional lenslet array design. The lenslet array has a square cross sectional shape with a three by three configuration. The lenslets are arranged in three rows, where each row comprises three lenslets. Alternative configurations may be possible by varying the number of rows, and/or the number of lenslets in each row, such as a nine by eleven array, a seven by nine array, or any other suitable combinations.

In this example each lenslet has a square aperture, thus an appropriate cross sectional shape for the resulting lenslet array may be rectangular or square. However, the lenslets may have a rectangular aperture shape, or it may have other aperture shapes such as a circle, oval, pentagon, hexagon, etc.

The appropriate cross sectional shape of the lenslet array may be determined by a number of factors, such as the shape of the lenslet aperture, the cross sectional shape of the light source, the cross sectional shape of the dental light irradiation device body, the cross sectional shape of the desired light patch produced by the dental light irradiation device, etc. In order for the lenslet array to take on various cross sectional shapes, the number of lenslets across all rows may vary in number for each row, and the number of rows of lenslets may vary in number.

FIG. 3A shows a top view of a honeycomb shaped lenslet array design. In this example each lenslet has a hexagon shaped aperture.

FIG. 3B shows an example of a pseudo circular lenslet array where each lenslet has a triangular shaped aperture.

The lenslet array can also be a single dimensional array. The single dimensional lenslet array can be normal to the body of the dental light irradiation device, and can have any suitable number of lenslets in the single dimension.

Figure 4:
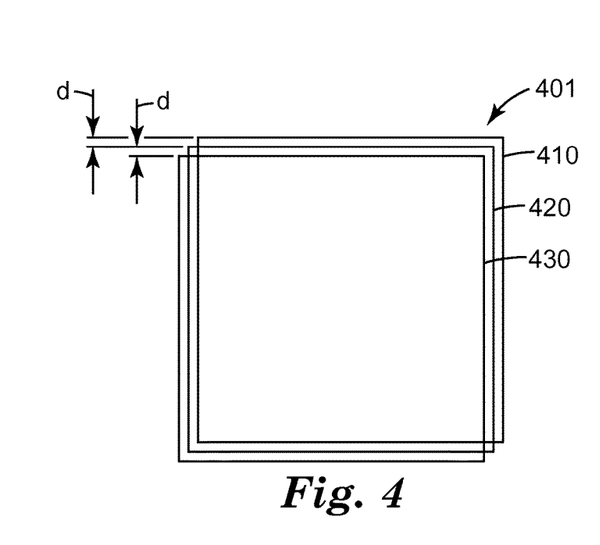
FIG. 4 is a top view of the composite light patch created by the lenslet array of FIG. 3C.
Figure 4A:
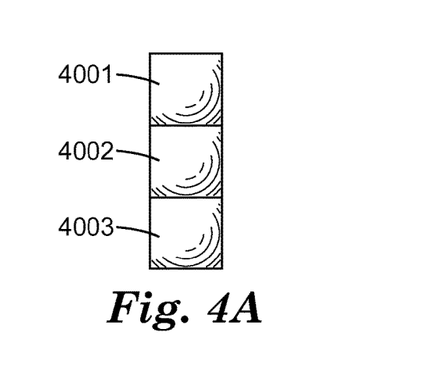
FIG. 4A is a top view of a one-dimensional lenslet array.

FIG. 4A shows a top view of a one-dimensional lenslet array with three lenslets 4001, 4002, 4003. In this example the lenslets have a square aperture. However, as previously described, the aperture of the lenslets may be of other shapes.

The lenslet array creates a composite light patch that has a size larger than the size of the light source at a finite distance away from the lenslet array.

Figure 4B:
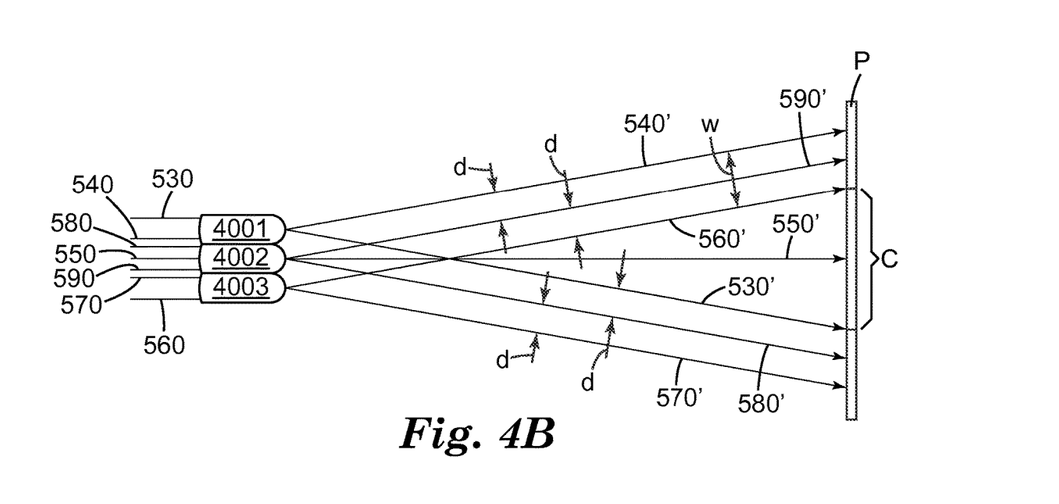
FIG. 4B is a side view of a simplified illustration of light beam paths modified by the three lenslet array of FIG. 4A.

FIG. 4B shows a side view of a simplified illustration of light beam paths modified by the three lenslet array of FIG. 4A. Light beams 530 and 540 represent light beams that enter lenslet 4001 at the lenslet's upper and lower edges. Light beams 580 and 590 represent light beams that enter lenslet 4002 at the lenslet's upper and lower edges. Light beams 560 and 570 represent light beams that enter lenslet 4003 at the lenslet's upper and lower edges. The incident angles of light beams 530, 580, and 570 upon the respective lenslets are substantially the same. The incident angles of light beams 540, 590, and 560 upon the respective lenslets are substantially the same. Light beam 550 enters the lenslet 4002 along the lenslet's optical axis and retains its original path exiting the lenslet 4002 as 550'.

Lenslets in the lenslet array focus the light beams and then diverge the light beams. Corresponding to light beams 530, 580, 570, 540, 590, 560 that are incident upon the lenslet array, light beams 530', 580', 570', 540', 590', 560' are the respective divergent light beams exiting the lenslet array. Light beams 530', 580' and 570' travel in substantially parallel paths, separated by a distance d. Light beams 540', 590' and 560' travel in substantially parallel paths, separated by a distance d.

Each lenslet produces a real image of its entrance aperture as a light patch. The lenslet array produces a composite light patch P that includes all individual light patches produced by individual lenslets. Composite light patch P may be of a dimension that closely matches the dimension of the site needing restoration. Each individual light patch overlaps with at least one other light patch formed by another lenslet.

For example, the light patches formed by the lenslets 4001 and 4002 overlap between light beams 590' and 530'. The light patches formed by the lenslets 4002 and 4003 overlap between light beams 560' and 580'. The light patches formed by the lenslets 4001 and 4003 overlap between light beams 560' and 530'. The regions between light beams 540' and 590', between 580' and 570' have no overlap. The light patches formed by all three lenslets fully overlap in the central region between light beams 560' and 530', forming a fully overlapped region C. The region C has uniform intensity. The remaining regions in the light patch are partially overlapped regions and are along the edges of the composite light patch P.

As the light beams exit the lenslet array and travel along their divergent paths, with the increase in distance from the light source the fully overlapped region C increases in size. Because the light beams along the edges of the composite light patch travel in substantially parallel paths, the partially overlapped regions remain relatively the same size while the fully overlapped region C grows relatively bigger.

The distance d between light beams 540', 590' and 560', as well as the distance between light beams 530', 580' and 570', are essentially the distance between the optical axis of adjacent lenslets. The width W of the region of partial overlap is d multiplied by (the number n of lenslets in the array minus 1).

$$W=d*(n-1)$$

In order to maximize the size of the fully overlapped region C and minimize the partially overlapped regions, it is advantageous to minimize the distance between the optical axis of adjacent lenslets. This can be accomplished by minimizing the aperture dimensions of the lenslets. In other words, keep the size of the lenslets small.

Therefore, the overall result is the maximization of the fully overlapped region C, and minimization of regions of less uniformity at the edges of the composite light patch P, thus creating a light patch of uniform intensity at the restoration site.

Figure 4C:
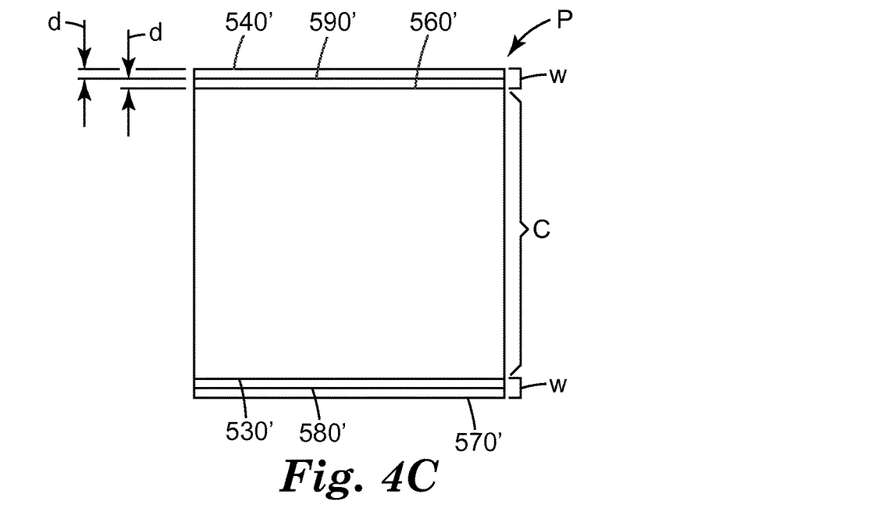
FIG. 4C is a top view of a composite light patch emitted by the dental light irradiation device employing the lenslet array of FIG. 4A.

FIG. 4C shows a top view of a composite light patch emitted by the dental light irradiation device employing the lenslet array of FIG. 4A.

The composite light patch P may have more uniform intensity at the fully overlapped region C compared to the edges, due to the fact light patches formed by individual lenslets do not fully overlap at the edges. However, when the apertures of the lenslets are small, d and W are kept to a minimum, differences in intensity profile between the fully overlapped region C and the edges are minimal, and thus the composite light patch exhibits properties similar to one of uniform intensity.

Although the illustrations 4A, 4B, 4C show the operation of a three lenslet single dimensional array, the general operating principles apply to lenslet arrays comprising any number of lenslets and various configurations, either as one-dimensional lenslet arrays or two-dimensional lenslet arrays.

Figure 4D:
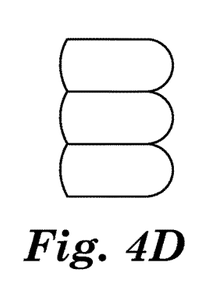
FIG. 4D is a side view of the three lenslet array of FIG. 4A.

FIG. 4D is a side view of the three lenslet array of FIG. 4A.

Figure 4E:
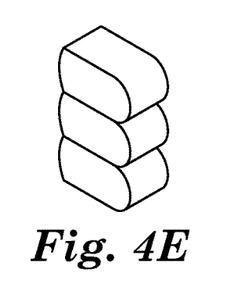
FIG. 4E is a top perspective view of the three lenslet array of FIG. 4A.

FIG. 4E is a top perspective view of the three lenslet array of FIG. 4A.

Figure 5:
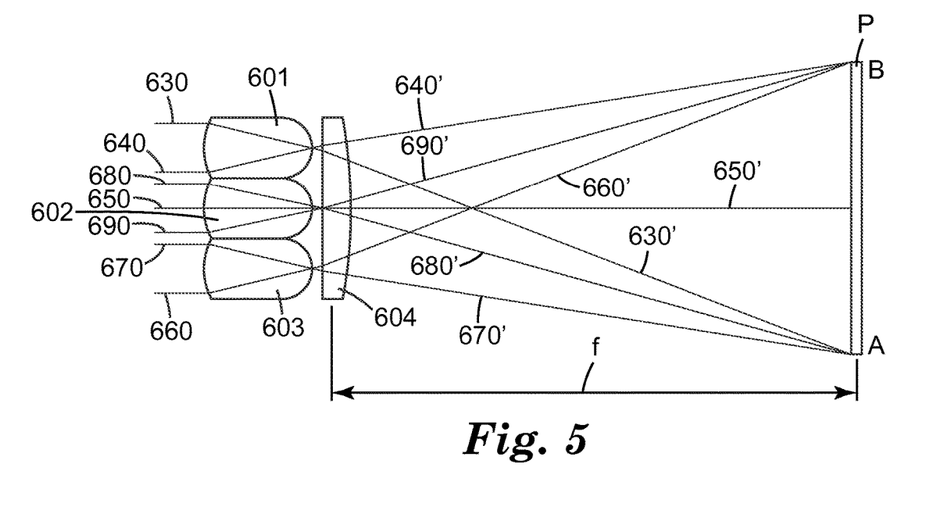
FIG. 5 is a side view of a simplified illustration of light beam paths modified by a three lenslet array and an optional relay lens.

FIG. 5 shows a side view of a simplified illustration of light beam paths modified by a three lenslet array and an optional relay lens 604.

The lenslet array is composed of three lenslets 601, 602, and 603. Light beams 630 and 640 represent light beams that enter lenslet 601 at the lenslet's upper and lower edges. Light beams 680 an 690 represent light beams that enter lenslet 602 at the lenslet's upper and lower edges. Light beams 660 an 670 represent light beams that enter lenslet 603 at the lenslet's upper and lower edges.

The incident angles of light beams 630, 680, and 670 upon the respective lenslets are substantially the same. The incident angles of light beams 640, 690, and 660 upon the respective lenslets are substantially the same. Light beam 650 enters lenslet 602 along the optical axis of the lenslet 602 and retains its original path exiting the lenslet 602 as 650'. Light beam 650 also travels along the optical axis of the relay lens 604 and its travel path is unaffected by the relay lens 604.

Lenslets in the lenslet array focus light beams and then diverge the light beams, as illustrated in FIG. 4B. Corresponding to light beams 630, 680, 670, 640, 690, 660 that are incident upon the lenslet array, light beams 630', 680', 670', 640', 690', 660' are the respective divergent light beams exiting the lenslet array. Prior to entering relay lens 604, light beams 630', 680' and 670' travel in substantially parallel paths, and light beams 640', 690' and 660' travel in substantially parallel paths.

Relay lens 604 converges light beams falling outside the fully overlapped region C to a point, thus eliminates any partially overlapped regions in the resulting light patch. This creates a light patch of uniform intensity. As illustrated in FIG. 6, relay lens 604 converges light beams 630', 680' and 670' to a single point A located on the focal plane of relay lens 604. Relay lens 604 also converges light beams 640', 690' and 660' to another single point B located on the focal plane of relay lens 604. Relay lens 604 is designed to converge to a single point light beams that it receives that travel along substantially parallel paths.

As a result, the composite light patch has no regions along its edges where the individual light patches produced by individual lenslets partially overlap. All individual light patches fully overlap and the resulting composite light patch P exhibits uniform intensity in its entire region.

In either the embodiment of FIG. 4B or FIG. 5, the dimensions of the composite light patch P should closely match the dimensions of the area needing restoration. For example, for curing a dental restoration on an adult tooth the light patch P may be approximately a 11.0 mm by 11.0 mm square, or a 15.6 mm diameter circle. The dimensions may be larger for individuals with larger than normal teeth. The dimensions may be smaller for children's teeth, or for individuals with smaller than normal teeth.

Figure 6A:
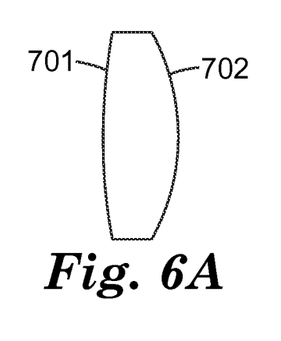
FIGS. 6A-6C are various embodiments of the optional relay lens.
Figure 6B:
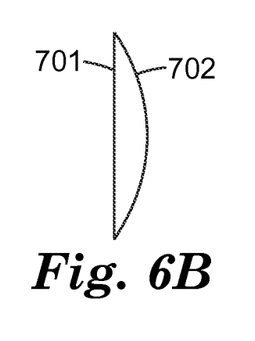
Figure 6C:
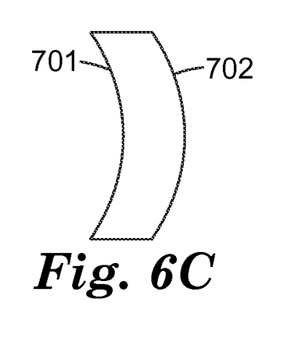

FIGS. 6A-6C show various embodiments of the optional relay lens. The relay lens may be made from a transparent material, with a refractive index greater than 1. The material may be optical glass or plastic, or any other type of suitable transparent material. The relay lens has two surfaces, a front surface 701 and a rear surface 702 that are opposite to each other. The relay lens is placed such that the front surface 701 is proximal to the lenslet array, and light beams exiting the lenslet array enters the relay lens at the front surface 701. Light beams then exit the relay lens at the real surface 702. The front surface 701 and rear surface 702 may be identical to each other or may be different from each other. However, the rear surface should always be convex.

FIG. 6A shows an example of the relay lens with a convex front surface and a convex rear surface. The curvatures of the front convex surface and the rear convex surface are different. FIG. 6B shows an example of the relay lens with a flat front surface and a convex rear surface. FIG. 6C shows an example of the relay lens with a concave front surface and a convex rear surface. The relay lens should be large enough to capture light beams exiting the lenslet array. The relay lens can be placed at any location within the dental light irradiation device body along the optical path between the lenslet array and the light deflecting mechanism or the cover glass.

What is claimed is:

1. A light irradiation device for emitting a light patch of uniform intensity, comprising:
    a housing;
    a light source within the housing emitting light beams;
    a relay lens having a front relay lens surface and a rear relay lens surface opposite the front relay lens surface; and
    an array of transparent lenslets within the housing, each of the lenslets of the array having a front lenslet convex surface and a rear lenslet convex surface opposite the front lenslet convex surface;
    wherein the front lenslet convex surface has a first focal point having a first focal length, f1, on a principal plane of the rear lenslet convex surface, and the rear lenslet convex surface has a second focal point having a second focal length, f2;

wherein f1 is different from f2;

wherein the light beams enter the transparent lenslets at the front lenslet convex surface and exit the transparent lenslets at the rear lenslet convex surface; and wherein the light beams enter the relay lens at the front relay lens surface and exit the relay lens at the rear relay lens surface, and the exiting light beams overlap each other forming a light patch of uniform intensity in a fully overlapped region of the overlapping light beams, wherein the overlapping light beams have no partially overlapping regions.

2. The light irradiation device of claim 1, wherein $0<(½)f1<f2<f1$.

3. The light irradiation device of claim 1, wherein each lenslet has an aperture with a dimension of 5 to 100 times smaller than a dimension of the light patch.

4. The light irradiation device of claim 1, wherein the front lenslet convex surface has a radius of 0.05 mm to 50 mm.

5. The light irradiation device of claim 1, wherein the rear lenslet convex surface has a radius of 0.05 mm to 50 mm.

6. The light irradiation device of claim 1, wherein the rear relay lens surface is convex.

7. The light irradiation device of claim 1, wherein the light patch has uniform intensity in its entire region.

8. The light irradiation device of claim 1, wherein the dimensions of the light patch are at least a 11 mm by 11 mm square or at least a 15.6 mm diameter circle.

9. The light irradiation device of claim 1, further comprising a fold mirror or a 45 degree prism located on a side of the relay lens opposite the lenslets.

10. The light irradiation device of claim 1, wherein the light source is a collimated LED or a laser.

11. The light irradiation device of claim 6, wherein the front relay lens surface is convex.

12. The light irradiation device of claim 6, wherein the front relay lens surface is flat.

13. The light irradiation device of claim 6, wherein the front relay lens surface is concave.

* * * * *